US007745226B2

(12) United States Patent
Clarke et al.

(10) Patent No.: US 7,745,226 B2
(45) Date of Patent: Jun. 29, 2010

(54) METHODS FOR DETECTING VITAMIN D METABOLITES

(75) Inventors: Nigel Clarke, Oceanside, CA (US); Brett Holmquist, Mission Viejo, CA (US); Kwang-Ja Lee, Irvine, CA (US); Richard E. Reitz, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 1007 days.

(21) Appl. No.: 11/101,166

(22) Filed: Apr. 6, 2005

(65) Prior Publication Data

US 2006/0228808 A1 Oct. 12, 2006

(51) Int. Cl.
*G01N 24/10* (2006.01)
(52) U.S. Cl. ...................................... 436/131; 436/173
(58) Field of Classification Search .................. 436/131, 436/173
See application file for complete search history.

(56) References Cited

U.S. PATENT DOCUMENTS

| | | | |
|---|---|---|---|
| 5,772,874 | A | 6/1998 | Quinn et al. |
| 5,795,469 | A | 8/1998 | Quinn et al. |
| 5,919,368 | A | 7/1999 | Quinn et al. |
| 5,968,367 | A | 10/1999 | Quinn et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Köster |
| 6,977,143 | B1 | 12/2005 | Caulfield et al. |
| 7,087,395 | B1 | 8/2006 | Garrity et al. |
| 2004/0235193 | A1 | 11/2004 | Soldin |
| 2006/0094125 | A1 | 5/2006 | Singh et al. |
| 2006/0228808 | A1 | 10/2006 | Clarke et al. |
| 2006/0228809 | A1 | 10/2006 | Clarke et al. |

FOREIGN PATENT DOCUMENTS

| | | |
|---|---|---|
| WO | WO 96/18618 | 6/1996 |
| WO | WO 2007/039193 | 4/2007 |
| WO | WO 2007/139956 | 12/2007 |

OTHER PUBLICATIONS

Coldwell et al., "Mass Fragmentographic Assay for 25-Hydroxyvitamin D in Plasma Without Derivatization: Enhanced Sensitivity for Metabolites of Vitamins D2 and D3 After Pre-column Dehydration", Journal of Mass Spectrometry, 30:348-356, 1995.
Maunsell et al., "Routine Isotope-Dilution Liquid Chromatography-Tandem Mass Spectrometry Assay for Simultaneous Measurement of the 25-Hydroxy Metabolites of Vitamins D2 and D2", Clinical Chemistry, 51:9 1683-1690, 2005.
Odrzywolska et al., "Convergent Synthesis, Chiral HPLC, and Vitamin D Receptor Affinity of Analogs of 1,25-Dihydroxycholecalciferol", Chirality, 11:249-255, 1999.
Watson et al., "Analysis of Vitamin D and its Metabolites using Thermospray Liquid Chromatography/Mass Spectrometry", Biomedical Chromatography, vol. 5, 153-160, 1991.
Yeung et al., "Characterization of the Metabolic Pathway of 1,25-Dihydroxy-16-Ene Vitamin D3 in Rat Kidney By On-Line High Performance Liquid Chromatography-Electrospray Tandem Mass Spectrometry", Biochemical Pharmacology, vol. 49, No. 8, pp. 1099-1110, 1995.
International Search Report for PCT Application PCT/US2006/12539.
Armas et. al., Vitamin D2 Is Much Less Effective than Vitamijn D3 in Humans, J. Clin. Endocrinol. Metab. 89:5387-5391 (2004).
Higashi T, et al., Simultaneous Determination of 25-Hydroxyvitamin $D^2$ and 25-Hydroxyvitamin $D^3$ in Human Plasma by Liquid Chromatography-Tandem Mass Spectrometry Employing Derivatization with a Cookson-Type Reagent, Biol Pharm Bull. 24(7):738-43, (2001).
Higashi T, et al., Characterization of urinary metabolites of vitamin $D_3$ in man under physiological conditions using liquid chromatography-tandem mass spectrometry, J Pharm Biomed Anal. 29(5):947-55 (2002).
Higashi T, et al., Characterization of new conjugated metabolites in bile of rats administered 24,25-dihydroxyvitamin $D_3$ and 25-hydroxyvitamin $D_3$, Steroids. 65(5):281-94 (2000).
Kissmeyer and Sonne, Sensitive analysis of 1α,25-dihydroxyvitamin $D_3$ in biological fluids by liquid chromatography-tandem mass spectrometry, J Chromatogr A. 935(1-2):93-103 (2001).
Merchant and Weinberger, Recent advancements in surface-enhanced laser desorption/ionization-time of flight-mass spectrometry, *Electrophoresis* 21:1164-77 (2000).
Salm et al., The Quantification of Sirolimus by High-Performance Liquid Chromatography-Tandem Mass Spectrometry and Microparticle Enzyme Immunoassay in Renal Transplant Recipients, *Clin. Therapeutics* 22 Supl. B:B71-B85 (2000).
Taylor et al., Simultaneous Quantification of Tacrolimus and Sirolimus in Human Blood, by High-Performance Liquid Chromatography—Tandem Mass Spectrometry, *Therapeutic Drug Monitoring* 22:608-12 (2000).
Wright et al., Proteinchip® surface enhanced laser desorption/ionization (SELDI) mass spectrometry: a novel protein biochip technology for detection of prostate cancer biomarkers in complex protein mixtures, *Prostate Cancer and Prostatic Diseases* 2:264-76 (1999).
Yeung B, et al., Characterization of viatmin $D_3$ metabolites using continuous-flow fast atom bombardment tandem mass spectrometry and high performance liquid chromatography, Chromatogr. 645(1):115-23 (1993).
Zimmer et al., Comparison of turbulent-flow chromatography with automated solid-phase extraction in 96-well plates and liquid-liquid extraction used as plasma sample preparation techniques for liquid chromatography-tandem mass spectrometry, *J. Chromatogr.* A 854:23-35 (1999).

(Continued)

*Primary Examiner*—Jill Warden
(74) *Attorney, Agent, or Firm*—Foley & Lardner LLP

(57) ABSTRACT

Provided are methods of detecting the presence or amount of a vitamin D metabolite in a sample using mass spectrometry. The methods generally comprise ionizing a vitamin D metabolite in a sample and detecting the amount of the ion to determine the presence or amount of the vitamin D metabolite in the sample. Also provided are methods to detect the presence or amount of two or more vitamin D metabolites in a single assay.

23 Claims, 4 Drawing Sheets

OTHER PUBLICATIONS

Vogeser et al., Candidate reference method for the quantification of circulating 25-Hydroxyvitamin $D_3$ by liquid chromatography-tandem mass spectrometry. Clinical Chemistry, 50(8): 1415-1417, 2004.

International Search Report for PCT Patent Application No. PCT/US2008/084709.

Bartolucci, et al., Liquid chromatography tandem mass spectrometric quantitation of sulfamethazine and its metabolites: direct analysis of swine urine by triple quadrupole and by ion trap mass spectrometry, *Rapid Commun. Mass Spectrom*, 14:967-73, 2000.

Busch, A Glossary for Mass Spectrometry. Mass Spectrometry, 17(65): 526-534, 2002.

Coldwell et al., Stable isotope-labeled vitamin D, metabolites and chemical analogs: synthesis and use in mass spectrometric studies. Steroids, 55: 418-432, 1990.

Guo et al., Steroid profiles using liquid chromatography-Tandem mass spectrometry with atmospheric pressure photoionization source. Arch Pathol Lab Med., 128: 469-475, 2004.

Jemal, High-throughput quantitative bioanalysis by LC/MS/MS. Biomedical Chromatography. 14:422-429, 2000.

Jones et al., Current understanding of the molecular actions of Vitamin D. Physiological Reviews, 78(4): 1193-1231, 1998.

Jones and Makin, Vitamin Ds: Metabolites and Analogs. Chapter 2 in *Modern Chromatographic Analysis of Vitamins*, Third Edition, Revised and expanded, edited by Leenheer et al., New York: Marcel Dekker, Inc., 2002.

Miller and Portale, Genetic causes of rickets. Current Opinions in Pediatrics, 11:333-339, 1999.

Singh et al., C-3 epimers can account for a significant proportion of total circulating 25-hydroxyvitamin D in infants, complicating accurate measurement and interpretation of vitamin D status. The Journal of Clinical Endocrinology & Metabolism, 91(8): 3055-3061, 2006.

Tsugawa et al., Determination of 25-hydroxyvitamin D in human plasma using high=performance liquid chromatography-tandem mass spectrometry. Anal. Chem., 77(9): 3001-3007, 2005.

Vieth, Vitamin D supplementation, 25-hydroxyvitamin D concentrations, and safety. Am J Clin Nutr, 69:842-856, 1999.

Vieth et al., Age-related changes in the 25-hydroxyvitamin D versus parathyroid hormone relationship suggest a different reason why older adults require more Vitamin D. The Journal of Clinical Endocrinology & Metabolism, 88(1): 185-191, 2003.

Wharton and Bishop, Rickets. The Lancet, 362: 1389-1400, 2003.

Letter from Vicki G. Norton, Ph.D. Partner, Duane Morris LLP, Sep. 4, 2008 (originally cited in an Information Disclosure Statement on Oct. 15, 2008 for U.S. Appl. No. 10/977,121).

Extended European Search Report for EPO Patent Application No. 06749272.8-2404.

Jones et al., Biological activity of 1,25-Dihydroxyvitamin $D_2$ in the Chick. Biochemistry, 15(3): 713-716, 1976.

Kissmeyer et al., Sensitive analysis of 1α, 25-dihydroxyvitamin $D_3$ in biological fluids by liquid chromatography-tandem mass spectrometry. Journal of Chromatography A, 935(2001) 93-103.

Tsugawa et al., Determination of 25-hydroxyvitamin D in human plasma using high-performance liquid chromatography-tandem mass spectrometry. Anal. Chem., 77:3001-3007, 2005.

Watson and Setchell, Analysis of Vitamin D and its metabolites using thermospray liquid chromatography/Mass spectrometry. Biomedical Chromatography, 5:153-160, 1991.

ial roles in the positive regulation of calcium ($Ca^{2+}$)
METHODS FOR DETECTING VITAMIN D METABOLITES

FIELD OF THE INVENTION

The invention relates to the detection of vitamin D metabolites. In a particular aspect, the invention relates to methods for detecting vitamin D metabolites by mass spectrometry.

BACKGROUND OF THE INVENTION

Vitamin D is an essential nutrient with important physiological roles in the positive regulation of calcium ($Ca^{2+}$) homeostasis. Vitamin D can be made de novo in the skin by exposure to sunlight or it can be absorbed from the diet. There are two forms of vitamin D; vitamin $D_2$ (ergocalciferol) and vitamin $D_3$ (cholecalciferol). Vitamin $D_3$ is the form synthesized de novo by animals. It is also a common supplemented added to milk products and certain food products produced in the United States. Both dietary and intrinsically synthesized vitamin $D_3$ must undergo metabolic activation to generate the bioactive metabolites. In humans, the initial step of vitamin $D_3$ activation occurs primarily in the liver and involves hydroxylation to form the intermediate metabolite 25-hydroxycholecalciferol (calcifediol; $25OHD_3$). Calcifediol is the major form of Vitamin $D_3$ in the circulation. Circulating $25OHD_3$ is then converted by the kidney to form 1,25-dihydroxyvitamin $D_3$ (calcitriol; $1,25(OH)_2D_3$), which is generally believed to be the metabolite of Vitamin $D_3$ with the highest biological activity.

Vitamin $D_2$ is derived from fungal and plant sources. Many over-the-counter dietary supplements contain ergocalciferol (vitamin $D_2$) rather than cholecalciferol (vitamin $D_3$). Drisdol, the only high-potency prescription form of vitamin D available in the United States, is formulated with ergocalciferol. Vitamin $D_2$ undergoes a similar pathway of metabolic activation in humans as Vitamin $D_3$, forming the metabolites $25OHD_2$ and $1,25(OH)_2D_2$. Vitamin $D_2$ and vitamin $D_3$ have long been assumed to be biologically equivalent in humans, however recent reports suggest that there may be differences in the bioactivity and bioavailability of these two forms of vitamin D (Armas et. al., (2004) J. Clin. Endocrinol. Metab. 89:5387-5391).

Measurement of vitamin D, the inactive vitamin D precursor, is rare in clinical settings and has little diagnostic value. Rather, serum levels of 25-hydroxyvitamin $D_3$ and 25-hydroxyvitamin $D_2$ (total 25-hydroxyvitamin D; "25OHD") are a useful index of vitamin D nutritional status and the efficacy of certain vitamin D analogs. Therefore, the measurement of 25OHD is commonly used in the diagnosis and management of disorders of calcium metabolism. In this respect, low levels of 25OHD are indicative of vitamin D deficiency associated with diseases such as hypocalcemia, hypophosphatemia, secondary hyperparathyroidism, elevated alkaline phosphatase, osteomalacia in adults and rickets in children. In patients suspected of vitamin D intoxication, elevated levels of 25OHD distinguishes this disorder from other disorders that cause hypercalcemia.

Measurement of $1,25(OH)_2D$ is also used in clinical settings, however, this test has a more limited diagnostic usefulness than measurements of 25OHD. Factors that contribute to limitations of the diagnostic values of $1,25(OH)_2D$ as an index of Vitamin D status include the precision of the endogenous regulation of renal production of the metabolite and its short half-life in circulation. However, certain disease states can be reflected by circulating levels of $1,25(OH)_2D$, for example kidney disease and kidney failure often result in low levels of $1,25(OH)_2D$. Elevated levels of $1,25(OH)_2D$ may be indicative of excess parathyroid hormone or can be indicative of certain diseases such as sarcoidosis or certain types of lymphomas.

Detection of vitamin D metabolites has been accomplished by radioimmunoassay with antibodies co-specific for $25OHD_2$ and $25OHD_3$. Because the current immunologically-based assays do not separately resolve $25OHD_2$ and $25OHD_3$, the source of any deficiency nutritional of vitamin D cannot be determined without resorting to other tests. More recently, reports have been published that disclose methods for detecting specific Vitamin D metabolites using mass spectrometry. For example Yeung B, et al., J Chromatogr. 1993, 645(1):115-23; Higashi T, et al., Steroids. 2000, 65(5):281-94; Higashi T, et al., Biol Pharm Bull. 2001, 24(7):738-43; and Higashi T, et al., J Pharm Biomed Anal. 2002, 29(5):947-55 disclose methods for detecting various vitamin D metabolites using liquid chromatography and mass spectrometry. These methods require that the metabolites be derivatized prior to detection by mass-spectometry. Methods to detect underivatized $1,25(OH)_2D_3$ by liquid chromatography/mass-spectrometry are disclosed in Kissmeyer and Sonne, J Chromatogr A. 2001, 935(1-2):93-103.

SUMMARY OF THE INVENTION

The present invention provides methods for detecting the presence or amount of a vitamin D metabolite in a test sample by mass spectrometry, including tandem mass spectometry. Preferably, the methods of the invention do not include derivatizing the sample or the vitamin D metabolites prior to the mass spectrometry analysis.

In one aspect the invention provides a method for determining the presence or amount of 25-hydroxyvitamin D in a biological sample. The method may include: (a) ionizing 25-hydroxyvitamin D, if present in the sample; and (b) detecting the presence or amount of the ion by mass spectrometry, wherein the presence or amount of the ion is related to the presence or amount of 25-hydroxyvitamin D in the test sample. In some preferred embodiments, the ionization step (a) may include (i) ionizing 25-hydroxyvitamin D, if present in the sample, to produce a 25-hydroxyvitamin D ion; (ii) isolating the 25-hydroxyvitamin D ion by mass spectrometry to provide a precursor ion; and (iii) effecting a collision between the isolated precursor ion and an inert collision gas to produce at least one fragment ion detectable in a mass spectrometer. In certain embodiments the 25-hydroxyvitamin D is 25-hydroxyvitamin $D_3$, in other related embodiments the 25-hydroxyvitamin D is 25-hydroxyvitamin $D_2$.

In another aspect, the invention provides a method for determining the presence or amount of 1,25-dihydroxyvitamin $D_2$ in a biological sample. The method may include: (a) ionizing the purified 1,25-dihydroxyvitamin $D_2$, if present in the sample, and (b) detecting the presence or amount of the ion by mass spectrometry, wherein the presence or amount of the ion is related to the presence or amount of 1,25-dihydroxyvitamin $D_2$ in the test sample. In certain embodiments, the ionization step (a) may include (i) ionizing 1,25-dihydroxyvitamin $D_2$, if present in the sample to produce a 1,25-dihydroxyvitamin $D_2$ ion; (ii) isolating the 1,25-dihydroxyvitamin $D_2$ ion by mass spectometry to provide a precursor ion; and (iii) effecting a collision between the isolated precursor ion and an inert collision gas to produce at least one fragment ion detectable in a mass spectrometer.

In another aspect the invention provides a method for determining the presence or amount of two or more vitamin D metabolites in a test sample in a single assay. The method includes ionizing the vitamin D metabolites to generate ions specific for each of the vitamin D metabolites of interest and detecting the presence or amount of the ions by mass spectrometry, wherein the presence or amount of the ions is related to the presence or amount of the vitamin D metabolites in the test sample. Preferably, the method does not involve derivatizing the samples or the vitamin D metabolites prior to analysis by mass spectrometry. In certain embodiments the mass spectrometry analysis of the method is tandem mass spectrometry.

As used herein, the term "vitamin D metabolite" refers to any vitamin D analog or any chemical species related to vitamin D. Vitamin D metabolites may include analogs of, or a chemical species related to, vitamin $D_2$ or vitamin $D_3$. Vitamin D metabolites may be found in the circulation of an animal and/or may be generated by a biological organism, such as an animal, or by biotransformation of vitamin $D_2$ or vitamin $D_3$. Vitamin D metabolites may be metabolites of naturally occurring forms of vitamin D or may be metabolites of synthetic vitamin D analogs. In certain embodiments a vitamin D metabolite is one or more compounds selected from the group consisting of 25-hydroxyvitamin $D_3$, 25-hydroxyvitamin $D_2$, 1,25-dihydroxyvitamin $D_3$ and 1,25-dihydroxyvitamin $D_2$.

Purification in the context of the methods of the invention does not refer to removing all materials from the sample other than the analyte(s) of interest. Instead, purification refers to a procedure that enriches the amount of one or more analytes of interest relative to one or more other components of the sample. In preferred embodiments, purification can be used to remove one or more interfering substances, e.g., one or more substances that would interfere with detection of an analyte ion by mass spectrometry.

As used herein, "biological sample" refers to any sample from a biological source. As used herein, "body fluid" means any fluid that can be isolated from the body of an individual. For example, "body fluid" may include blood, plasma, serum, bile, saliva, urine, tears, perspiration, and the like.

As used herein, "derivatizing" means reacting two molecules to form a new molecule. Derivatizing agents may include isothiocyanate groups, dinitro-fluorophenyl groups, nitrophenoxycarbonyl groups, and/or phthalaldehyde groups.

As used herein, "chromatography" refers to a process in which a chemical mixture carried by a liquid or gas is separated into components as a result of differential distribution of the solutes as they flow around or over a stationary liquid or solid phase.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column.

As used herein, the term "gas chromatography" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase As used herein, "mass spectrometry" (MS) refers to an analytical technique to identify compounds by their mass. MS technology generally includes (1) ionizing the compounds and potentially fractionating the compounds to form charged compounds; and (2) detecting the molecular weight of the charged compound and calculating a mass-to-charge ratio (m/z). The compound may be ionized and detected by any suitable means. A "mass spectrometer" generally includes an ionizer and an ion detector.

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g. ammonia) is subjected to electron impact, and analyte ions are formed by the interaction of reagent gas ions and analyte molecules.

The term "fast atom bombardment" as used herein refers to methods in which a beam of high energy atoms (often Xe or Ar) impacts a non-volatile test sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine.

The term "field desorption" as used herein refers to methods in which a non-volatile test sample is placed on an ionization surface, and an intense electric field is used to generate analyte ions.

The term "ionization" as used herein refers to the process of generating an analyte ion having a net electrical charge equal to one or more electron units. Negative ions are those having a net negative charge of one or more electron units, while positive ions are those having a net positive charge of one or more electron units.

The term "operating in negative ion mode" refers to those mass spectrometry methods where negative ions are detected. Similarly, "operating in positive ion mode" refers to those mass spectrometry methods where positive ions are detected.

The term "desorption" as used herein refers to the removal of an analyte from a surface and/or the entry of an analyte into a gaseous phase.

The term "about" as used herein in reference to quantitative measurements, refers to the indicated value plus or minus 10%.

DETAILED DESCRIPTION OF THE INVENTION

Figure 1:
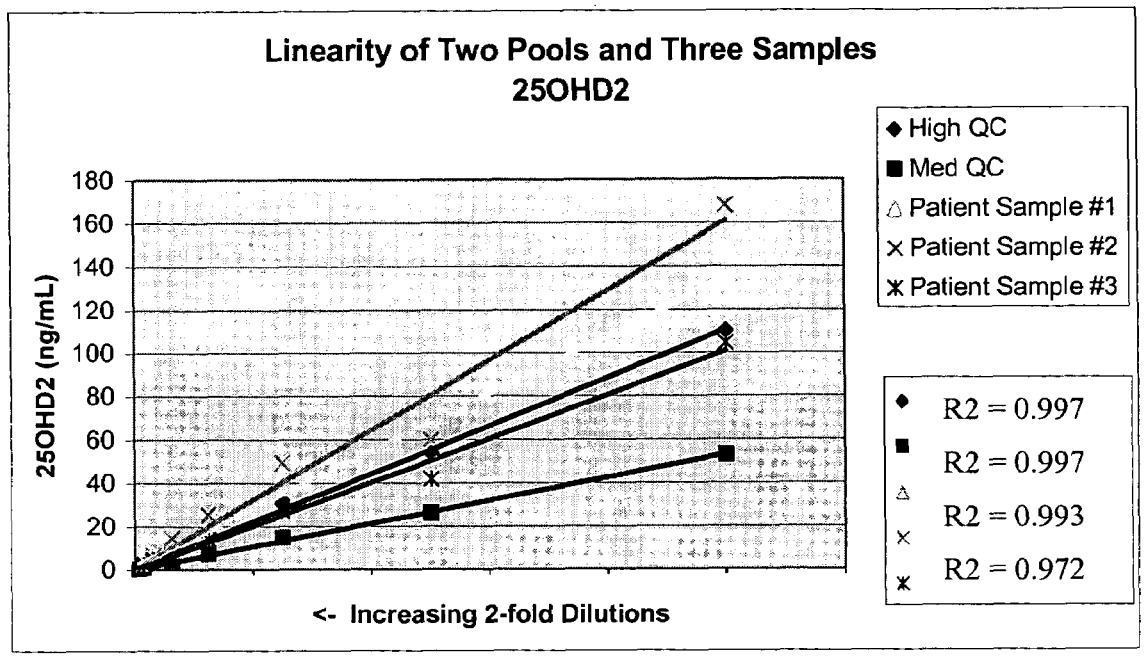
FIG. 1 shows the linearity of the quantification of $25OHD_2$ in samples serially diluted with the 25OHD diluent using the LC-MS/MS assay.

Disclosed are methods for detecting the presence or amount of one or more vitamin D metabolites in a test sample. In certain aspects the method involves ionizing the vitamin D metabolites and detecting the ion by mass spectrometry, wherein the presence of the ion is related to the presence or amount of the vitamin D metabolite in the test sample. In related aspects, the method may include (a) purifying a vitamin D metabolite, if present in the test sample, by chromatography, (b) ionizing the purified vitamin D metabolite and (c) detecting the presence or amount of the ion, wherein the presence or amount of the ion is related to the presence or amount of the vitamin D metabolite in the test sample. In preferred embodiments, the ionizing step (b) may comprise (i) ionizing a vitamin D metabolite, if present in the sample, to produce an ion; (ii) isolating the vitamin D metabolite ion by mass spectometry to provide a precursor ion; and (iii) effecting a collision between the isolated precursor ion and an inert collision gas to produce at least one fragment ion detectable in a mass spectrometer. In certain embodiments at least one fragment ion is detected, wherein the presence or amount of the fragment ion is related to the presence or amount of the vitamin D metabolite in the test sample. In some embodiments, the methods of the invention can be used to detect and quantify two or more vitamin D metabolites in a single assay.

Suitable test samples include any sample that might contain the analyte of interest and/or one or more metabolites or precursors thereof. For example, samples obtained during the manufacture of an analyte can be analyzed to determine the composition and yield of the manufacturing process. In certain embodiments, a sample is a biological sample; that is, a sample obtained from any biological source, such as an animal, a cell culture, an organ culture, etc. Particularly preferred are samples obtained from a human, such as a blood, plasma, serum, hair, muscle, urine, saliva, tear, cerebrospinal fluid, or other tissue sample. Such samples may be obtained, for example, from a patient; that is, a living person presenting themselves in a clinical setting for diagnosis, prognosis, or treatment of a disease or condition.

Samples may be processed or purified to obtain preparations that are suitable for the desired type of chromatography and/or for analysis by mass spectrometry. Various procedures may be used for this purpose depending on the type sample or the type of chromatography. Examples include filtration, extraction, precipitation, centrifugation, dilution, combinations thereof and the like. Protein precipitation is one preferred method of preparing a liquid biological sample, such as serum or plasma, for chromatography. In a preferred embodiment, one volume of the liquid sample is added to four volumes of methanol. This results in the precipitation of most protein while vitamin D metabolites are fully soluble in the resulting supernatant. The samples can then be centrifuged to separate the liquid supernatant from the pellet. The resultant supernatants can then be applied to liquid chromatography and mass spectrometry analysis. Preferably, sample preparation does not involve the use of a derivitization agent. Therefore the methods of the invention preferably do not include a derivatization step prior to analysis of the sample by mass spectrometry. Thus, the methods allow the detection and quantification directly of ions of the desired vitamin D metabolites rather than ions of a derivatized form of the vitamin D metabolites.

The sample, or the processed sample, may be purified prior to analysis by mass spectrometry. Such purification, or sample clean-up, refers to a procedure that enriches of one or more analytes of interest relative to one or more other components of the sample. Typically, chromatography, preferably liquid chromatography, more preferably high performance liquid chromatography is used for the purification. In preferred embodiments the chromatography is not gas chromatography. Preferably, the methods of the invention are performed without subjecting the test samples, or the vitamin D metabolites of interest, to gas chromatography prior to mass spectrometric analysis.

Various methods have been described involving the use of HPLC for sample clean-up prior to mass spectrometry analysis. See, e.g., Taylor et al., *Therapeutic Drug Monitoring* 22:608-12 (2000) (manual precipitation of blood samples, followed by manual C18 solid phase extraction, injection into an HPLC for chromatography on a C18 analytical column, and MS/MS analysis); and Salm et al., *Clin. Therapeutics* 22 Supl. B:B71-B85 (2000) (manual precipitation of blood samples, followed by manual C18 solid phase extraction, injection into an HPLC for chromatography on a C18 analytical column, and MS/MS analysis). One of skill in the art can select HPLC instruments and columns that are suitable for use in the invention. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties such as vitamin D metabolites. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In the method, the test sample is applied to the column at the inlet port, eluted with a solvent or solvent mixture, and discharged at the outlet port. Different solvent modes may be selected for eluting the analytes. For example, liquid chromatography may be performed using a gradient mode, an isocratic mode, or a polytyptic (i.e. mixed) mode. In preferred embodiments, HPLC is performed on a multiplexed analytical HPLC system with a C18 solid phase using isocratic separation with 100% methanol as the mobile phase.

Recently, high turbulence liquid chromatography ("HTLC"), also called high throughput liquid chromatography, has been applied for sample preparation prior to analysis by mass spectrometry. See, e.g., Zimmer et al., *J. Chromatogr.* A 854:23-35 (1999); see also, U.S. Pat. Nos. 5,968,367; 5,919,368; 5,795,469; and 5,772,874, each of which is hereby incorporated by reference in its entirety. Traditional HPLC analysis relies on column packings in which laminar flow of the sample through the column is the basis for separation of the analyte of interest from the test sample. The skilled artisan will understand that separation in such columns is a diffusional process. In contrast, it is believed that turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the vitamin D metabolite of interest. In such embodiments samples may be extracted using an HTLC extraction cartridge which captures the analyte, then eluted and chromatographed on a second HTLC column prior to ionization. Because the steps involved in these two HTLC procedures can be linked in an automated fashion, the requirement for operator involvement during the purification of the analyte can be minimized.

The terms "mass spectrometry" or "MS" as used herein refer to methods of filtering, detecting, and measuring ions based on their mass-to-charge ratio, or "m/z." In general, one or more molecules of interest, such as a vitamin D metabolites, are ionized and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000), each of which is hereby incorporated by reference in its entirety, including all tables, figures, and claims.

The mass spectrometer will include an ion source for ionizing the fractionated sample and creating charged molecules for further analysis. For example ionization of the sample may be performed by electrospray ionization (ESI), atmospheric pressure chemical ionization (ACPI), photoionization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., m/z). Preferably, the negatively charged ions are analyzed. Suitable analyzers for determining mass-to-charge ratios include quadropole analyzers, ion traps analyzers, and time-of-flight analyzers. The ions may be detected by using several detection modes. For example, selected ions may be detected (i.e., using a selective ion monitoring mode (SIM)), or alternatively, ions may be detected using a scanning mode. Preferably, the mass-to-charge ratio is determined using a quadropole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

One can often enhance the resolution of the MS technique by employing "tandem mass spectrometry," or "MS/MS." In this technique, a first, or parent, or precursor, ion generated from a molecule of interest can be filtered in an MS instrument, and these parent ions subsequently fragmented to yield one or more second, or daughter, or fragment, ions that are then analyzed in a second MS procedure. By careful selection of parent ions, only ions produced by certain analytes are passed to the fragmentation chamber, where collision with atoms of an inert gas to produce these daughter ions. Because both the parent and daughter ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps can be combined in methods known as "MS/MS"." Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each m/z over a given range (e.g., 100 to 1000 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards can be run with the samples, and a standard curve constructed based on ions generated from those standards. Using such a standard curve, the relative abundance of a given ion can be converted back into an absolute amount of the original molecule. Numerous other methods for relating the presence or amount of an ion to the presence or amount of the original molecule will be well known to those of ordinary skill in the art.

One or more steps of the methods of the invention can be performed using automated machines. In certain embodiments, one or more purification steps are performed on line, and more preferably all of the purification and mass spectroscopy steps may be performed in an on line fashion.

In a particularly preferred embodiment vitamin D metabolites using MS/MS as follows. The flow of liquid solvent from a chromatographic column, possibly comprising one or more vitamin D metabolites, enters the heated nebulizer interface of a LC-MS/MS analyzer and the solvent/analyte mixture is converted to vapor in the heated tubing of the interface. The analytes (i.e. vitamin D metabolites), contained in the nebulized solvent, are ionized by the corona discharge needle of the interface, which applies a large voltage to the nebulized solvent/analyte mixture. The ions pass through the orifice of the instrument and enter the first quadrupole. Quadrupoles 1 and 3 (Q1 and Q3) are mass filters, allowing selection of ions based on their mass to charge ratio (m/z). Quadrupole 2 (Q2) is the collision cell, where ions are fragmented. The first quadrupole of the mass spectrometer (Q1) selects for molecules with the mass to charge ratios of the specific vitamin D metabolites to be analyzed. Ions with the correct m/z ratios of the vitamin D metabolites are allowed to pass into the collision chamber (Q2), while unwanted ions with any other m/z collide with the sides of the quadrupole and are eliminated. Ions entering Q2 collide with neutral Argon gas molecules and fragment. This process is called Collision Activated Dissociation (CAD). The fragment ions generated are passed into quadrupole 3 (Q3), where the fragment ions of the desired vitamin D metabolites are selected while other ions are eliminated. As ions collide with the detector they produce a pulse of electrons that are converted to a digital signal. In some embodiments the mass/charge ratio (m/z) for the 25-hydroxyvitamin $D_3$ precursor ion is about 383.16, the m/z for the 25-hydroxyvitamin $D_3$ fragment ion is about 211.35, the m/z for the 25-hydroxyvitamin $D_2$ precursor ion is about 395.30 and the m/z for the 25-hydroxyvitamin $D_2$ fragment ions are about 179.1, 209.20, 251.30. In embodiments where the samples are spiked with hexadeuterated 25OHD$_3$, $^6$D-25OHD$_3$, for use as an internal standard the mass/charge ratio (m/z) for the $^6$D-25OHD$_3$ precursor ion is about 389.2 and the m/z for the 25-hydroxyvitamin D$_3$ fragment ion is about 211.30. Mass spectrometry instruments can vary slightly in determining the mass of a given analyte. Thus, the term "about" in the context of mass of an ion or the m/z of an ion refers to +/−0.5 atomic mass units. The acquired data is relayed to a computer, which plots counts of the ions collected versus time. The resulting mass chromatograms are similar to chromatograms generated in traditional HPLC methods. The areas under the peaks are determined and calibration curves are constructed by plotting standard concentration versus peak area ratio of analyte/internal standard. Using the calibration curves, the concentrations of the vitamin D metabolites are quantified in the samples.

The following examples serve to illustrate the present invention. These examples are in no way intended to limit the scope of the invention.

EXAMPLES

Example 1

Determination of 25-hydroxyvitamin D$_3$ and 25-hydroxyvitamin D$_2$ by LC-MS/MS Using a Perkin-Elmer MultiProbe II (S/N 432400) robotic liquid handler, human serum samples were first extracted using a protein precipitation method by adding 42.5 μl of serum of serum 170 μl of methanol (1:4 ratio of serum: methanol) in a 96-well plate format. For validation-related experiments, the methanol was spiked with hexadeuterated 25OHD$_3$ ($^6$D-25OHD$_3$) as an internal standard. The 96 well plates were centrifuged which resulted in the precipitation of most protein in a pellet, while the vitamin D metabolites remained in solution in the supernatant. The supernatants were then transferred to an HPLC autosampler for loading to the LC-MS/MS analyzer.

LC-MS/MS was performed using a Thermo Finnigan LC-MS/MS analyzer (Thermo Finnigan Quantum TSQ (S/N: TQU00655)) with an atmospheric pressure chemical ionization (APCI) source used as the detector. Liquid chromatography was performed with a Cohesive Technologies Aria TX-4 (S/N: SJCTX409) LC system with Waters Symmetry C18 5 μm 4.6×50 mm columns. The multiplexed analytical HPLC system uses a C18 solid phase with an isocratic separation using 100% methanol as the mobile phase. The autosampler injected 50 μL of extracted sample supernatant onto the HPLC column. After the analytes eluted and the detector window completed acquisition, the system was washed with 85% Mobile phase A and then re-equilibrated with Mobile phase B for a run time of 5 minutes. Mobile phase A was 0.1% formic acid in HPLC-grade water and mobile phase B was 100% methanol.

The flow of liquid solvent from the HTLC entered the heated nebulizer interface of the Thermo Finnigan LC-MS/MS analyzer. The solvent/analyte mixture was first converted to vapor in the heated tubing of the interface. The analytes, contained in the nebulized solvent, were ionized (a positive charge added) by the corona discharge needle of the interface, which applies a large voltage to the nebulized solvent/analyte mixture. The ions pass through the orifice of the instrument and enter the first quadrupole. Quadrupoles 1 and 3 (Q1 and Q3) are mass filters, allowing selection of ions based on their mass to charge ratio (m/z). Quadrupole 2 (Q2) is the collision cell, where ions are fragmented.

The first quadrupole of the mass spectrometer (Q1) selected for molecules with the mass to charge ratios of (pro- tonated and dehydrated) 25OHD$_2$, 25OHD$_3$ and $^6$D-25OHD$_3$. Ions with these m/z ratios (see table below) were allowed to pass into the collision chamber (Q2), while unwanted ions with any other m/z collide with the sides of the quadrupole and are eliminated. Ions entering Q2 collide with neutral Argon gas molecules and fragment. This process is called Collision Activated Dissociation (CAD). The fragment ions generated are passed into quadrupole 3 (Q3), where the fragment ions of 25OHD$_2$, 25OHD$_3$ and $^6$D-25OHD$_3$ were selected (see table below) and other ions are eliminated. The following mass transitions were used for detection and quantitation during validation:

TABLE 1

Mass transitions for selected vitamin D metabolites

| Compound | Precursor Ion (m/z) | Fragment Ions (m/z) |
|---|---|---|
| 25OHD$_2$ | 395.30 | 179.10, 251.30, 209.20 |
| 25OHD$_3$ | 383.16 | 211.35 |
| $^6$D-25OHD$_3$ | 389.20 | 211.30 |

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods.

Area ratios of the analyte and internal standard (Hexadeuterated 25-Hydroxyvitamin D3, $^6$D-25OHD$_3$) peaks were used to construct calibration curves, which were then used to calculate analyte concentrations. Using the calibration curves, the concentrations of 25OHD$_2$ and 25OHD3 were quantitated in the patient samples.

Example 2

Intra-Assay and Inter-Assay Precision

Three levels of spiked serum were made from patient pools (Medium and High Pools) and stripped serum from Golden West Biologicals, Product #SP1070 (Low Pool). Each pool was spikes with stock solutions of 25OHD$_2$ and/or 25OHD$_3$ to bring analyte concentrations to the desired levels. The target concentrations of the control pools used for these determinations were: Low; 20-25 ng/mL, medium; 45-55 ng/mL and High; 100-110 ng/mL for each analyte. Twenty aliquots from each level were analyzed in a single assay using the LC-MS/MS protocols described in example 1. The following precision values were determined:

TABLE 2

Intra-Assay Variation: 25-Hydroxyvitamin D$_2$ (25OHD$_2$)

|   | Low 092804-L | Medium 092804-M | High 092804-H |
|---|---|---|---|
| 1 | 26.5 | 46.4 | 103.3 |
| 2 | 23.2 | 51.1 | 96.7 |
| 3 | 23.1 | 52.4 | 107.8 |
| 4 | 21.6 | 50.3 | 104.5 |
| 5 | 26.3 | 47.5 | 96.2 |
| 6 | 25.1 | 54.4 | 98.5 |
| 7 | 25.9 | 54.6 | 100.0 |
| 8 | 21.9 | 50.1 | 110.1 |
| 9 | 23.4 | 50.8 | 97.6 |
| 10 | 23.5 | 53.2 | 105.1 |
| 11 | 22.2 | 52.9 | 105.9 |

TABLE 2-continued

Intra-Assay Variation: 25-Hydroxyvitamin D$_2$ (25OHD$_2$)

| | Low 092804-L | Medium 092804-M | High 092804-H |
|---|---|---|---|
| 12 | 24.0 | 54.6 | 94.5 |
| 13 | 26.2 | 49.4 | 93.4 |
| 14 | 24.1 | 59.0 | 113.0 |
| 15 | 25.8 | 52.9 | 112.4 |
| 16 | 23.9 | 59.2 | 113.4 |
| 17 | 29.5 | 52.4 | 107.7 |
| 18 | 24.2 | 50.0 | 115.5 |
| 19 | 19.8 | 53.5 | 114.9 |
| 20 | 26.3 | 60.2 | 126.6 |
| Average (ng/mL) | 24.3 | 52.7 | 105.9 |
| Std Dev | 2.2 | 3.6 | 8.6 |
| CV (%) | 9.0 | 6.9 | 8.1 |

TABLE 3

Intra-Assay Variation: 25-Hydroxyvitamin D$_3$ (25OHD$_3$)

| | Low 092804-L | Medium 092804-M | High 092804-H |
|---|---|---|---|
| 1 | 22.7 | 43.6 | 99.1 |
| 2 | 22.4 | 45.3 | 93.5 |
| 3 | 22.4 | 50.7 | 98.2 |
| 4 | 21.0 | 40.1 | 95.9 |
| 5 | 21.8 | 41.5 | 82.0 |
| 6 | 20.8 | 42.2 | 97.4 |
| 7 | 22.9 | 50.1 | 96.0 |
| 8 | 19.0 | 42.0 | 106.7 |
| 9 | 21.8 | 44.2 | 96.6 |
| 10 | 23.4 | 49.5 | 94.9 |
| 11 | 21.8 | 46.5 | 97.9 |
| 12 | 20.7 | 49.9 | 87.1 |
| 13 | 25.4 | 44.7 | 85.5 |
| 14 | 24.5 | 48.0 | 101.5 |
| 15 | 25.1 | 45.8 | 101.5 |
| 16 | 22.5 | 52.0 | 104.7 |
| 17 | 29.2 | 45.9 | 107.7 |
| 18 | 19.5 | 49.3 | 107.6 |
| 19 | 18.1 | 49.6 | 109.4 |
| 20 | 24.8 | 49.3 | 116.1 |
| Average (ng/mL) | 22.5 | 46.5 | 99.0 |
| Std Dev | 2.5 | 3.5 | 8.4 |
| CV (%) | 11.2 | 7.5 | 8.5 |

The spiked serum pools described above were also analyzed to determine inter-assay precision. Four aliquots from each level were analyzed over five different assays using the LC-MS/MS protocols described in example 1. The following precision values were determined:

TABLE 4

Inter-Assay Variation: 25-Hydroxyvitamin D$_2$ (25OHD$_2$)

| | Low 092804-L | Medium 092804-M | High 092804-H |
|---|---|---|---|
| 1 | 26.5 | 46.4 | 103.3 |
| 2 | 23.2 | 51.1 | 96.7 |
| 3 | 23.1 | 52.4 | 107.8 |
| 4 | 21.6 | 50.3 | 104.5 |
| 5 | 26.3 | 47.5 | 96.2 |
| 6 | 25.1 | 54.4 | 98.5 |
| 7 | 25.9 | 54.6 | 100.0 |
| 8 | 21.9 | 50.1 | 110.1 |
| 9 | 23.4 | 50.8 | 97.6 |
| 10 | 23.5 | 53.2 | 105.1 |
| 11 | 22.2 | 52.9 | 105.9 |
| 12 | 24.0 | 54.6 | 94.5 |

TABLE 4-continued

Inter-Assay Variation: 25-Hydroxyvitamin D$_2$ (25OHD$_2$)

| | Low 092804-L | Medium 092804-M | High 092804-H |
|---|---|---|---|
| 13 | 26.2 | 49.4 | 93.4 |
| 14 | 24.1 | 59.0 | 113.0 |
| 15 | 25.8 | 52.9 | 112.4 |
| 16 | 23.9 | 59.2 | 113.4 |
| 17 | 29.5 | 52.4 | 107.7 |
| 18 | 24.2 | 50.0 | 115.5 |
| 19 | 19.8 | 53.5 | 114.9 |
| 20 | 26.3 | 60.2 | 126.6 |
| Average (ng/mL) | 24.3 | 52.7 | 105.9 |
| Std Dev | 2.2 | 3.6 | 8.6 |
| CV (%) | 9.0 | 6.9 | 8.1 |

TABLE 5

Inter-Assay Variation: 25-Hydroxyvitamin D$_3$ (25OHD$_3$)

| | Low 092804-L | Medium 092804-M | High 092804-H |
|---|---|---|---|
| 1 | 22.7 | 43.6 | 99.1 |
| 2 | 22.4 | 45.3 | 93.5 |
| 3 | 22.4 | 50.7 | 98.2 |
| 4 | 21.0 | 40.1 | 95.9 |
| 5 | 21.8 | 41.5 | 82.0 |
| 6 | 20.8 | 42.2 | 97.4 |
| 7 | 22.9 | 50.1 | 96.0 |
| 8 | 19.0 | 42.0 | 106.7 |
| 9 | 21.8 | 44.2 | 96.6 |
| 10 | 23.4 | 49.5 | 94.9 |
| 11 | 21.8 | 46.5 | 97.9 |
| 12 | 20.7 | 49.9 | 87.1 |
| 13 | 25.4 | 44.7 | 85.5 |
| 14 | 24.5 | 48.0 | 101.5 |
| 15 | 25.1 | 45.8 | 101.5 |
| 16 | 22.5 | 52.0 | 104.7 |
| 17 | 29.2 | 45.9 | 107.7 |
| 18 | 19.5 | 49.3 | 107.6 |
| 19 | 18.1 | 49.6 | 109.4 |
| 20 | 24.8 | 49.3 | 116.1 |
| Average (ng/mL) | 22.5 | 46.5 | 99.0 |
| Std Dev | 2.5 | 3.5 | 8.4 |
| CV (%) | 11.2 | 7.5 | 8.5 |

Example 3

Analytical Sensitivity: Limit of Detection and Limit of Quantitation Studies

To determine the limit of detection of the assay, blank diluent was analyzed 17 times within a single run using the LC-MS/MS protocols described in example 1. The mean and standard deviation was then calculated. The limit of detection was calculated as 2 SD above the mean of the blank peak area ratio based on a back calculation of peak area ratio against the calibration curve. The limits of detection were as follows:

25OHD$_2$: 3.0 ng/mL

25OHD$_3$: 3.5 ng/mL

To determine the limit of quantitation atandard curves of 25OHD$_2$ and 25OHD$_3$ were run in quadruplicate over five assays using the LC-MS/MS protocols described in example 1. The ranges were 0, 2, 4, 8, 16, 32, 64 and 128 ng/mL. The analyzed concentrations were pooled and the statistical analysis was performed on values from 5 separate runs. The results of the study were as follows:

TABLE 6

Limit of Quantitation Study Results: 25-Hydroxyvitamin $D_2$ (25OHD$_2$)

| | #1 | #2 | #3 | #4 | #5 | Summary | |
|---|---|---|---|---|---|---|---|
| 0 ng/mL | −1.2 | −1.3 | −0.5 | −1.2 | −1.1 | Average (ng/mL) | −1.0 |
| | −1.1 | −1.4 | −0.9 | −1.3 | −0.7 | Standard Deviation | 0.6 |
| | −1.1 | −1.5 | −0.8 | NA | −2.6 | C of V (%) | 59.0 |
| | 0.4 | −1.7 | −0.6 | −0.5 | −0.6 | Accuracy (%) | N/A |
| 2 ng/mL | 3.1 | 2.3 | 2.0 | 2.1 | 3.3 | Average (ng/mL) | 1.9 |
| | 2.1 | 2.7 | 2.1 | 2.4 | 1.9 | Standard Deviation | 0.6 |
| | 1.1 | 1.9 | 1.9 | 0.9 | 1.3 | C of V (%) | 33.7 |
| | 1.2 | 1.1 | 2.1 | 1.8 | 1.4 | Accuracy (%) | 103.9 |
| 4 ng/mL | 3.5 | 3.9 | 5.0 | 4.5 | 4.8 | Average (ng/mL) | 3.9 |
| | 4.0 | 3.0 | 3.8 | 3.8 | 4.7 | Standard Deviation | 0.7 |
| | 3.6 | 2.9 | 2.8 | 3.1 | 2.0* | C of V (%) | 17.1 |
| | 4.1 | 4.6 | 4.5 | 4.4 | 3.7 | Accuracy (%) | 101.7 |
| 8 ng/mL | 10.2 | 9.1 | 9.1 | 8.8 | 9.8 | Average (ng/mL) | 8.6 |
| | 7.8 | 8.1 | 7.9 | 8.4 | 9.0 | Standard Deviation | 0.8 |
| | 8.6 | 8.3 | 7.4 | 8.4 | 7.5 | C of V (%) | 9.3 |
| | 10.2 | 8.4 | 8.0 | 8.1 | 8.6 | Accuracy (%) | 93.2 |
| 16 ng/mL | 16.0 | 14.8 | 14.4 | 16.7 | 18.3 | Average (ng/mL) | 16.0 |
| | 15.5 | 15.6 | 15.3 | 16.7 | 16.8 | Standard Deviation | 1.1 |
| | 16.6 | 16.7 | 16.8 | 15.8 | 15.2 | C of V (%) | 7.1 |
| | 14.1 | 17.6 | 16.1 | 16.7 | 14.1 | Accuracy (%) | 100.1 |
| 32 ng/mL | 31.3 | 39.9* | 29.9 | 33.2 | 32.7 | Average (ng/mL) | 31.8 |
| | 31.7 | 30.5 | 32.4 | 34.0 | 32.5 | Standard Deviation | 1.9 |
| | 29.5 | 31.2 | 30.2 | 35.7 | 28.7 | C of V (%) | 6.0 |
| | 32.9 | 34.7 | 32.4 | 30.8 | 29.2 | Accuracy (%) | 100.7 |
| 64 ng/mL | 66.5 | 62.2 | 68.5 | 62.6 | 68.8 | Average (ng/mL) | 64.6 |
| | 66.6 | 67.8 | 67.3 | 58.9 | 61.5 | Standard Deviation | 3.2 |
| | 64.4 | 61.4 | 63.7 | 63.5 | 61.3 | C of V (%) | 4.9 |
| | 63.7 | 60.7 | 65.4 | 70.8 | 65.9 | Accuracy (%) | 99.1 |
| 128 ng/mL | 125.1 | 128.2 | 123.4 | 127.8 | 124.1 | Average (ng/mL) | 126.9 |
| | 127.6 | 134.4 | 127.3 | 128.4 | 132.1 | Standard Deviation | 3.5 |
| | 128.9 | 124.5 | 128.5 | 126.5 | 131.7 | C of V (%) | 2.8 |
| | 126.1 | 119.7 | 127.9 | 121.2 | 125.0 | Accuracy (%) | 100.8 |

TABLE 7

Limit of Quantitation Study Results: 25-Hydroxyvitamin $D_3$ (25OHD$_3$)

| | Day #1 (11/19/04-1) | Day #2 (11/19/04-2) | Day #3 (11/22/04-1) | Day #4 (11/23/04-1) | Day #5 (11/23/04-2) | Summary | |
|---|---|---|---|---|---|---|---|
| 0 ng/mL | −0.5 | −0.9 | −0.3 | 0.2 | −0.6 | Average (ng/mL) | −0.7 |
| | −0.7 | −1.3 | 0.3 | −1.1 | −1.0 | Standard Deviation | 0.6 |
| | 0.0 | −1.0 | −1.1 | −1.3 | 0.6 | C of V (%) | 86.4 |
| | −0.3 | −1.5 | −1.1 | −0.8 | −1.0 | Accuracy (%) | N/A |
| 2 ng/mL | 2.6 | 1.5 | 2.4 | 2.5 | 1.7 | Average (ng/mL) | 1.9 |
| | 1.7 | 0.9 | 3.2 | 2.2 | 1.9 | Standard Deviation | 0.6 |
| | 1.8 | 1.8 | 2.0 | 1.1 | 2.2 | C of V (%) | 31.4 |
| | 1.3 | 2.4 | 1.5 | 1.1 | 2.5 | Accuracy (%) | 104.7 |
| 4 ng/mL | 3.9 | 3.5 | 4.8 | 4.0 | 3.4 | Average (ng/mL) | 3.8 |
| | 3.0 | 4.1 | 3.1 | 3.9 | 3.8 | Standard Deviation | 0.8 |
| | 4.5 | 3.7 | 2.9 | 3.5 | 2.4 | C of V (%) | 19.7 |
| | 4.0 | 5.2 | 3.8 | 3.8 | 5.5 | Accuracy (%) | 104.1 |
| 8 ng/mL | 10.3 | 9.3 | 7.2 | 8.4 | 8.6 | Average (ng/mL) | 8.7 |
| | 10.6 | 8.5 | 7.2 | 10.0 | 9.6 | Standard Deviation | 1.1 |
| | 7.4 | 10.3 | 9.0 | 9.4 | 8.4 | C of V (%) | 13.1 |
| | 9.3 | 7.7 | 8.5 | 7.6 | 6.8 | Accuracy (%) | 91.9 |
| 16 ng/mL | 15.9 | 15.6 | 16.2 | 18.6 | 17.1 | Average (ng/mL) | 16.0 |
| | 13.8 | 16.3 | 14.0 | 17.2 | 15.3 | Standard Deviation | 1.4 |
| | 15.6 | 16.1 | 15.1 | 18.8 | 16.1 | C of V (%) | 8.5 |
| | 14.8 | 17.2 | 17.0 | 14.3 | 15.3 | Accuracy (%) | 99.9 |
| 32 ng/mL | 31.1 | 35.8 | 29.6 | 32.8 | 28.0 | Average (ng/mL) | 31.7 |
| | 30.8 | 29.9 | 31.8 | 33.0 | 32.8 | Standard Deviation | 1.9 |
| | 31.6 | 30.9 | 29.5 | 35.7 | 31.2 | C of V (%) | 6.2 |
| | 31.0 | 34.2 | 31.8 | 30.6 | 31.7 | Accuracy (%) | 101.0 |
| 64 ng/mL | 65.9 | 64.6 | 64.4 | 64.8 | 67.8 | Average (ng/mL) | 64.8 |
| | 67.4 | 62.9 | 62.4 | 60.7 | 57.2 | Standard Deviation | 3.1 |
| | 68.9 | 64.2 | 62.1 | 64.0 | 64.7 | C of V (%) | 4.8 |
| | 63.2 | 64.2 | 66.8 | 67.7 | 71.1 | Accuracy (%) | 98.8 |

TABLE 7-continued

Limit of Quantitation Study Results: 25-Hydroxyvitamin $D_3$ (25OHD$_3$)

| | Day #1 (11/19/04-1) | Day #2 (11/19/04-2) | Day #3 (11/22/04-1) | Day #4 (11/23/04-1) | Day #5 (11/23/04-2) | Summary | |
|---|---|---|---|---|---|---|---|
| 128 ng/mL | 128.9 | 124.5 | 126.4 | 125.3 | 122.8 | Average (ng/mL) | 127.1 |
| | 129.7 | 135.7 | 128.3 | 125.9 | 128.7 | Standard Deviation | 4.7 |
| | 125.5 | 123.3 | 127.2 | 127.7 | 135.4 | C of V (%) | 3.7 |
| | 121.3 | 121.8 | 137.8 | 121.4 | 124.1 | Accuracy (%) | 100.7 |

Example 5

Assay Reportable Range and Linearity

To establish the linearity of the vitamin D metabolite LC-MS/MS assay, the MultiProbe automated liquid handler robot independently constructed two standard curves by serially diluting a stock solution containing 128 ng/mL 25OHD$_2$ and 128 ng/mL 25OHD$_3$ in 25OHD diluent (5% Bovine Serum Albumin Fraction V dissolved in 0.01M PBS). The standard curve samples were analyzed using the LC-MS/MS protocols described in example 1. This process routinely produced standard curves with $R^2$ values of 0.99 or higher for each analyte for the range of 4-128 ng/mL.

Figure 2:
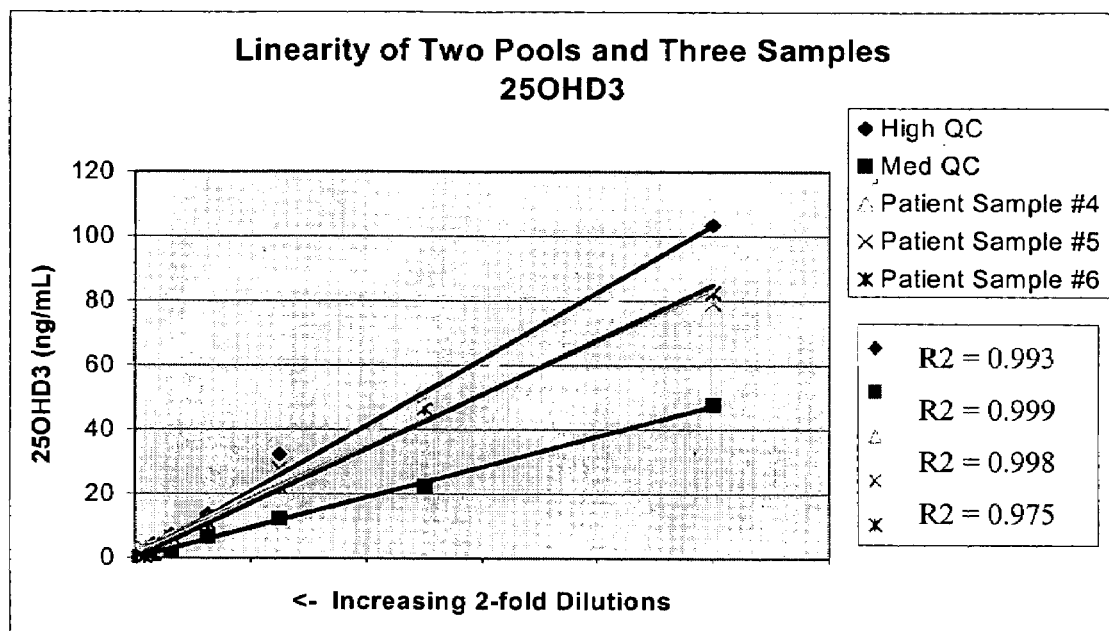
FIG. 2 shows the linearity of the quantification of $25OHD_3$ in samples serially diluted with the 25OHD diluent using the LC-MS/MS assay.

To determine whether patient samples can also be diluted in a linear fashion, a total of eight samples were serially diluted with 25OHD diluent. Two samples were patient pools (Medium and High Control Pools), three were patient samples with high 25OHD$_2$ values and three were patients with high 25OHD$_3$ values. All samples were analyzed using the LC-MS/MS protocols described in example 1. As shown in FIG. 1 and FIG. 2, each sample diluted in a linear fashion ($R^2$>0.98), demonstrating the suitability of 25OHD diluent for diluting patient samples.

Figure 3:
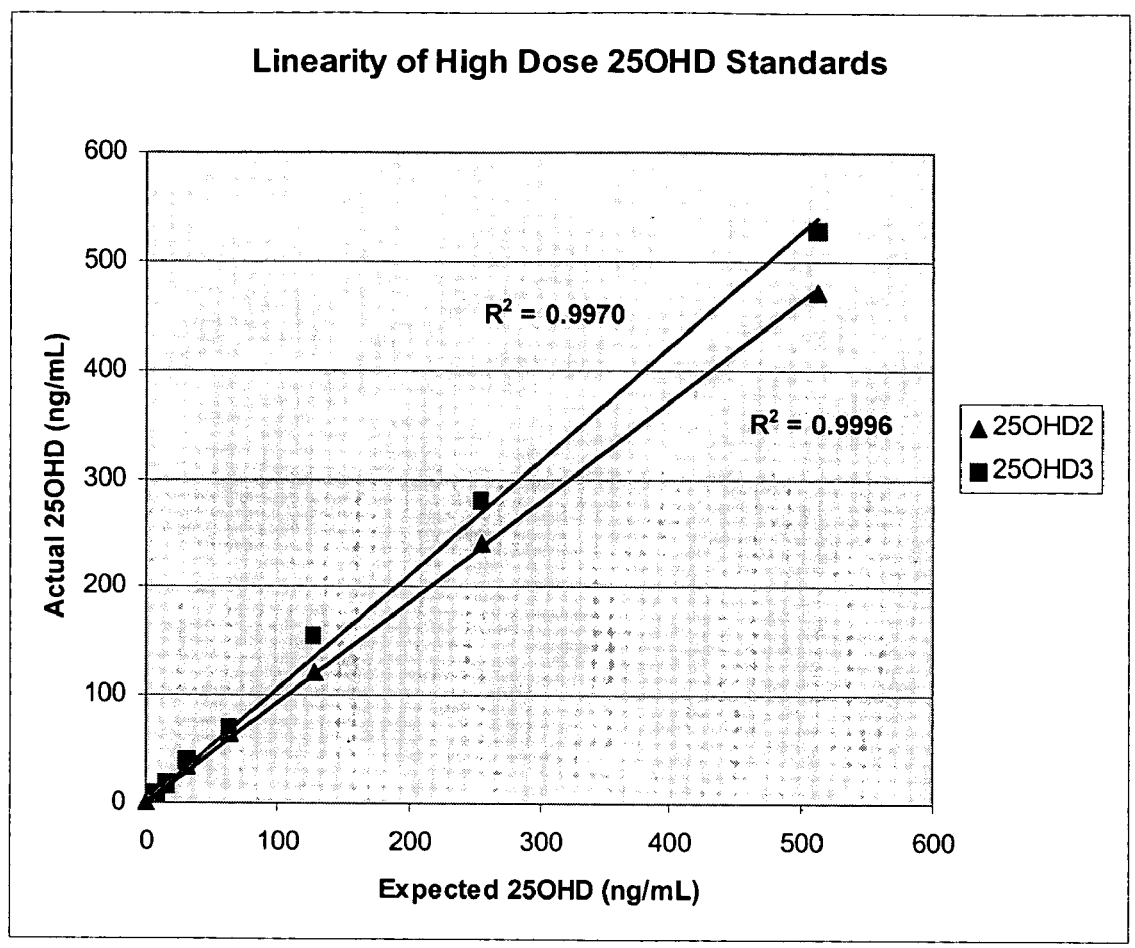
FIG. 3 shows the linearity of the quantification by LC-MS/MS of serially diluted samples spiked with of $25OHD_2$ and $25OHD_3$ to final concentrations of 512 ng/mL.

To demonstrate that elevated samples can be diluted into the linear range of the assay, aliquots of 25OHD diluent were spiked to 512 ng/mL each 25OHD$_2$ and 25HOD$_3$, then serially diluted to 8 ng/mL using the 25OHD diluent. Each sample was extracted and run in duplicate using the LC-MS/MS protocols described in example 1. As shown in FIG. 3, each of these curves was linear ($R^2$>0.99).

Example 6

Accuracy of LC-MS/MS Vitamin D Assay

The standards for 25OHD$_2$ and 25OHD$_3$ were quantified based upon the absorbance of the concentrated (10-50 μg/mL) stock solutions in the ultraviolet spectrum. The cis-triene chromophore present in all vitamin D compounds has a peak absorbance of 264 nm, which is dependent upon the analyte concentration. The molar extinction coefficient of 18.3 mM$^{-1}$cm$^{-1}$ was determined using purified, dessicated ergocalciferol and cholecalciferol and was used to determine the concentration of stock solutions for 25OHD$_2$ and 25OHD$_3$.

To determine the ability to recover vitamin D metabolites from spiked serum samples, three patient pools of known concentrations were spiked with two levels of 25OHD$_2$, 25OHD$_3$ and both 25OHD$_2$ and 25OHD$_3$ together. Each sample was extracted and run in duplicate using the LC-MS/MS protocols described in example 1. The recovery was calculated by dividing the expected result by the observed result.

TABLE 8

Recovery of 25-hydroxylated vitamin D metabolites from spiked samples.

| | 25OHD$_2$ (ng/mL) | 25OHD$_3$ (ng/mL) | 25OHD$_2$ (% Recovery) | 25OHD$_3$ (% Recovery) |
|---|---|---|---|---|
| Pool#1 | 58 | 51 | — | — |
| Pool#1 + 20 ng/mL 25OHD$_2$ | 75 | 52 | 104 | — |
| Pool#1 + 20 ng/mL 25OHD$_3$ | 52 | 68 | — | 105 |
| Pool#1 + 20 ng/mL of both | 72 | 68 | 109 | 105 |
| Pool#1 + 50 ng/mL 25OHD$_2$ | 104 | 50 | 105 | — |
| Pool#1 + 50 ng/mL 25OHD$_3$ | 56 | 109 | — | 93 |
| Pool#1 + 50 ng/mL of both | 104 | 110 | 104 | 92 |
| Pool#2 | 53 | 47 | — | — |
| Pool#2 + 20 ng/mL 25OHD$_2$ | 76 | 51 | 97 | — |
| Pool#2 + 20 ng/mL 25OHD$_3$ | 52 | 66 | — | 101 |
| Pool#2 + 20 ng/mL of both | 70 | 65 | 105 | 103 |
| Pool#2 + 50 ng/mL 25OHD$_2$ | 107 | 53 | 96 | — |
| Pool#2 + 50 ng/mL 25OHD$_3$ | 57 | 109 | — | 88 |
| Pool#2 + 50 ng/mL of both | 100 | 105 | 103 | 92 |
| Pool#3 | 53 | 47 | — | — |
| Pool#3 + 20 ng/mL 25OHD$_2$ | 69 | 44 | 106 | — |
| Pool#3 + 20 ng/mL 25OHD$_3$ | 55 | 75 | — | 90 |
| Pool#3 + 20 ng/mL of both | 74 | 69 | 98 | 97 |
| Pool#3 + 50 ng/mL 25OHD$_2$ | 96 | 48 | 107 | — |
| Pool#3 + 50 ng/mL 25OHD$_3$ | 53 | 114 | — | 85 |
| Pool#3 + 50 ng/mL of both | 105 | 113 | 98 | 85 |

Example 7

Comparison LC-MS/MS Vitamin D Metabolite Assay and RIA Procedures

Figure 4:
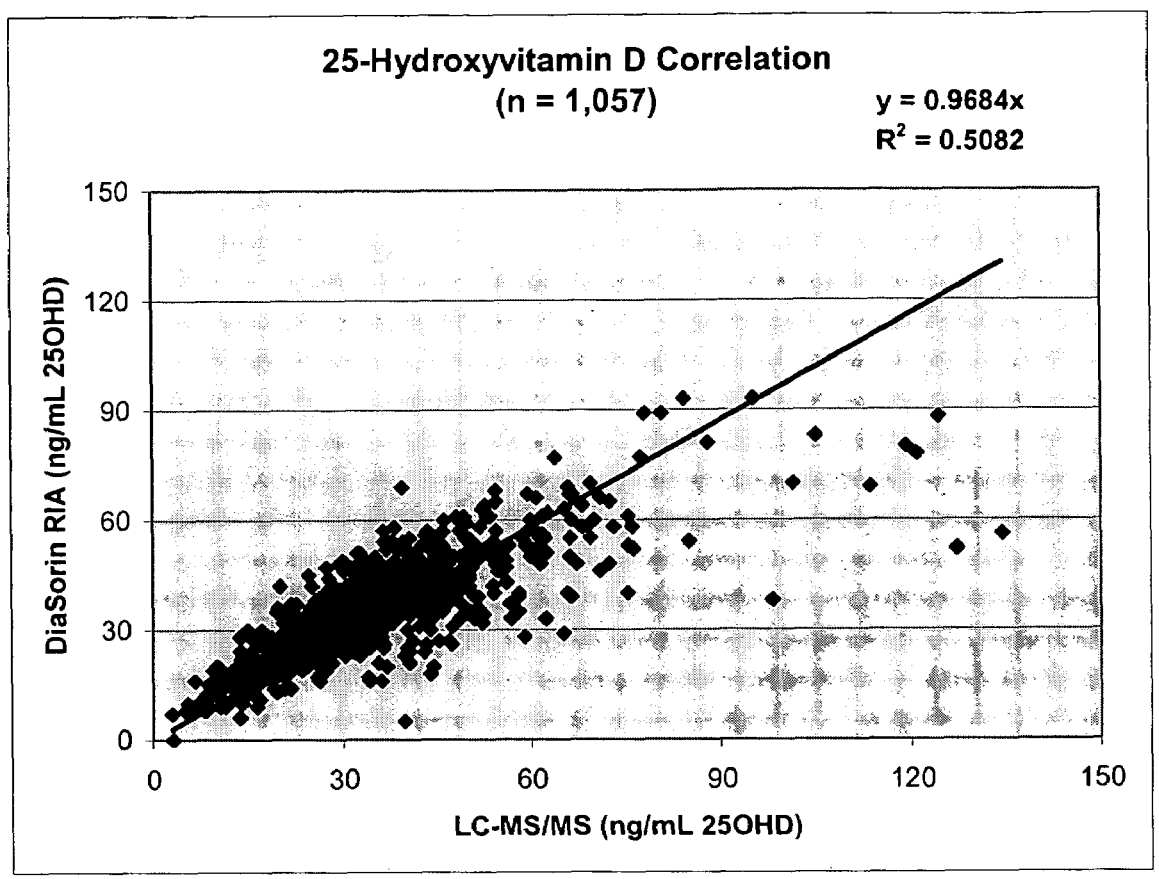
FIG. 4 shows the correlation between detection of total 25-hydroxyvitamin D using the LC-MS/MS method and a commercially available radioimmunoassay kit.

A total of 1,057 patient samples were assayed using the LC-MS/MS methods described in example 1 and using an RIA commercially available from DiaSorin and the data were compared. As shown in FIG. 4, for total 25OHD, the $R^2$ value was 0.5082 with a slope of 0.9684.

Example 8

Cross-Reactivity Studies

Samples were prepared by diluting various commercially available vitamin D metabolites and analogues at a concentration of 100 ng/mL in 25OHD diluent. Samples were extracted and run in duplicate using the LC-MS/MS methods described in example 1. None of the tested compounds had measurable signals detected in the 25OHD$_2$ and 25OHD$_3$ detection channels.

TABLE 9

Cross-Reactivity of the LC-MS/MS method with various vitamin D analogues and metabolites.

| | Compound Mass (Da) | Cross-Reactivity (25OHD$_2$) | Cross-Reactivity (25OHD$_3$) |
|---|---|---|---|
| 25-Hydroxyvitamin D$_2$ (25OHD$_2$) | 412 | (100%) | ND |
| 25-Hydroxyvitamin D$_3$ (25OHD$_3$) | 400 | ND | (100%) |
| Internal Standard ($^6$D-25OHD$_3$) | 406 | ND | ND |
| Vitamin D$_2$ (Ergocalciferol) | 396 | ND | ND |
| Vitamin D$_3$ (Cholecalciferol) | 384 | ND | ND |
| 1☐,25(OH)$_2$D$_2$ | 428 | ND | ND |
| 1☐,25(OH)$_2$D$_3$ | 416 | ND | ND |
| 25,26(OH)$_2$D$_3$ | 416 | ND | ND |
| 1☐(OH)D$_2$ (Doxercalciferol) | 412 | ND | ND |
| 1☐(OH)D$_3$ (Alfacalcidiol) | 400 | ND | ND |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A method for determining the presence or amount of 25-hydroxyvitamin D$_3$ in a biological sample, comprising:
   (a) ionizing said 25-hydroxyvitamin D$_3$, if present in said sample to produce a 25-hydroxyvitamin D$_3$ ion;
   (b) isolating said 25-hydroxyvitamin D$_3$ ion by mass spectrometry to provide a precursor ion having a mass/charge ratio (m/z) of about 383.2;
   (c) effecting a collision between the isolated precursor ion and an inert collision gas to produce at least one fragment ion detectable in a mass spectrometer; and
   (d) detecting the presence or amount of at least one of said precursor or fragment ions by mass spectrometry, wherein the presence or amount of said ion is related to the presence or amount of 25-hydroxyvitamin D$_3$ in said test sample;
   wherein said sample is purified by chromatography prior to said ionization step.

2. The method of claim 1, wherein said chromatography is liquid chromatography.

3. The method of claim 1, wherein said chromatography is high performance liquid chromatography (HPLC).

4. The method of claim 1, wherein said at least one 25-hydroxyvitamin D$_3$ fragment ion has an m/z of about 211.35.

5. A method for determining the presence or amount of 25-hydroxyvitamin D$_3$ and 25-hydroxyvitamin D$_2$ in a test sample in a single assay using tandem mass spectrometry, said method comprising:
   (a) ionizing said 25-hydroxyvitamin D$_3$ and 25-hydroxyvitamin D$_2$, if present in said sample, to generate ions specific for each of 25-hydroxyvitamin D$_3$ and 25-hydroxyvitamin D$_2$; and
   (b) detecting the presence or amount of at least one of said ions specific for each of 25-hydroxyvitamin D$_3$ and 25-hydroxyvitamin D$_2$ by mass spectrometry, wherein the presence or amount of said ions is related to the presence or amount of said 25-hydroxyvitamin D$_3$ and 25-hydroxyvitamin D$_2$ in said test sample; wherein at least one of said ions detected by mass spectrometry is an ion selected from the group consisting of ions having a mass/charge ration of about 211.35, 179.1, 209.20, and 251.30;
   wherein said sample is purified by chromatography prior to said ionization step.

6. The method of claim 5, wherein said chromatography is liquid chromatography.

7. The method of claim 5, wherein said chromatography is high performance liquid chromatography (HPLC).

8. The method of claim 5, wherein at least one of said 25-hydroxyvitamin D$_3$ ions has a mass/charge ratio (m/z) of about 383.16 and at least one of said 25-hydroxyvitamin $D_2$ ions has a mass/charge ratio (m/z) of about 395.30.

9. The method of claim 5, wherein at least one of said ions detected by mass spectrometry is an ion having a mass/charge ratio of about 211.35.

10. The method of claim 5, wherein at least one of said ions detected by mass spectrometry is an ion having a mass/charge ratio of about 179.1.

11. The method of claim 5, wherein at least one of said ions detected by mass spectrometry is an ion having a mass/charge ratio of about 209.20.

12. The method of claim 5, wherein at least one of said ions detected by mass spectrometry is an ion having a mass/charge ratio of about 251.30.

13. The method of claim 5, wherein the mass/charge ratio (m/z) for the 25-hydroxyvitamin $D_3$ precursor ion is about 383.16, the m/z for the 25-hydroxyvitamin $D_3$ fragment ion is about 211.35, the m/z for the 25-hydroxyvitamin $D_2$ precursor ion is about 395.30 and the m/z for the 25-hydroxyvitamin $D_2$ fragment ions include one or more ions selected from the group consisting of ions having a mass/charge ratio (m/z) of about 179.1, 209.20, and 251.30.

14. The method of claim 13, wherein the m/z for the 25-hydroxyvitamin $D_2$ fragment ions include an ion having a mass/charge ratio (m/z) of about 179.1

15. The method of claim 13, wherein the m/z for the 25-hydroxyvitamin $D_2$ fragment ions include an ion having a mass/charge ratio (m/z) of about 209.20.

16. The method of claim 13, wherein the m/z for the 25-hydroxyvitamin $D_2$ fragment ions include an ion having a mass/charge ratio (m/z) of about 251.30.

17. A method for determining the presence or amount of 25-hydroxyvitamin $D_2$ in a biological sample, comprising:

(a) ionizing said 25-hydroxyvitamin $D_2$, if present in said sample to produce a 25-hydroxyvitamin $D_2$ ion;

(b) isolating said 25-hydroxyvitamin $D_2$ ion by mass spectrometry to provide a precursor ion having a mass/charge ratio (m/z) of about 395.3;

(c) effecting a collision between the isolated precursor ion and an inert collision gas to produce at least one fragment ion detectable in a mass spectrometer; and (d) detecting the presence or amount of at least one of said precursor or fragment ions by mass spectrometry, wherein the presence or amount of said ion is related to the presence or amount of 25-hydroxyvitamin $D_2$ in said test sample;

wherein said sample is purified by chromatography prior to said ionization step.

18. The method of claim 17, wherein said chromatography is liquid chromatography.

19. The method of claim 17, wherein said chromatography is high performance liquid chromatography (HPLC).

20. The method of claim 17, wherein said at least one 25-hydroxyvitamin $D_2$ fragment ion comprises one or more ions selected from the group consisting of ions having an m/z of about 179.1, 209.20, and 251.30.

21. The method of claim 20, wherein said at least one 25-hydroxyvitamin $D_2$ fragment ion comprises an ion having an m/z of about 179.1.

22. The method of claim 20, wherein said at least one 25-hydroxyvitamin $D_2$ fragment ion comprises an ion having an m/z of about 209.20.

23. The method of claim 20, wherein said at least one 25-hydroxyvitamin $D_2$ fragment ion comprises an ion having an m/z of about 251.30.

* * * * *